United States Patent
Luthardt (12)

(10) Patent No.: US 6,431,871 B1
(45) Date of Patent: Aug. 13, 2002

(54) METHOD FOR THE COMPUTER-CONTROLLED PRODUCTION OF DENTURES

(76) Inventor: Ralph G. Luthardt, Goetheallee 17a, D-01309 Dresden (DE)

( * ) Notice: Subject to any disclaimer, the term of this patent is extended or adjusted under 35 U.S.C. 154(b) by 0 days.

(21) Appl. No.: 09/744,992

(22) PCT Filed: Aug. 23, 1999

(86) PCT No.: PCT/EP99/06170

§ 371 (c)(1),
(2), (4) Date: Apr. 11, 2001

(87) PCT Pub. No.: WO00/10482

PCT Pub. Date: Mar. 2, 2000

(30) Foreign Application Priority Data

Aug. 22, 1998 (DE) ........................ 198 38 238

(51) Int. Cl.[7] ................................. A61C 5/10
(52) U.S. Cl. ........................ 433/223; 433/54
(58) Field of Search ................. 433/24, 167, 171, 433/223, 54

(56) References Cited

U.S. PATENT DOCUMENTS

| | | |
|---|---|---|
| 5,368,478 A | 11/1994 | Andreiko et al. |
| 5,431,562 A | 7/1995 | Andreiko et al. |
| 5,447,432 A | 9/1995 | Andreiko et al. |
| 5,454,717 A | 10/1995 | Andreiko et al. |
| 5,456,600 A | 10/1995 | Andreiko et al. |
| 5,474,448 A | 12/1995 | Andreiko et al. |
| 5,542,842 A | 8/1996 | Andreiko et al. |
| 5,683,243 A | 11/1997 | Andreiko et al. |
| 5,800,174 A | 9/1998 | Andersson |

FOREIGN PATENT DOCUMENTS

| | | |
|---|---|---|
| DE | 19518702 | 11/1996 |
| EP | 0311214 | 4/1989 |

OTHER PUBLICATIONS

"Computermodellierter Zahnersatz mit dem Cicero–System", Phillip Journal 7–8/96—pp. 227–235.

Primary Examiner—Nicholas D. Lucchesi
(74) Attorney, Agent, or Firm—Dennison, Schultz & Dougherty

(57) ABSTRACT

The invention relates to a method for the computer-controlled production of dentures for restoring at least one tooth or jaw area, especially in terms of occlusal or incisal contact. The aim of the invention is to provide a simple means of producing dentures using CAD/CAM techniques, at the same time ensuring that the contact surfaces of the denture have the individual shape required so that absolutely no subsequent work is necessary. To this end, the inventive method comprises the following steps: forming an impression of the upper and lower jaw in order to produce casts of the same and co-ordinating them using an articulator; co-ordinating at least two points of reference on the upper jaw cast or the lower jaw cast or other selected points of reference with the axis of rotation of the articulator or with at least two points of reference allocated to the same, arranging the upper jaw cast and the lower jaw cast in a measuring device for determining the geometry of the tooth, jaw or jaw area being restored, the two points of reference being arranged in a predetermined position in relation to the system of co-ordinates of the measuring device in order to produce a virtual representation of the axis of rotation of the articulator or the at least two points of reference allocated to the same; digitising the upper and lower jaw casts; constructing the denture using CAD and manufacturing the denture using CAM.

13 Claims, 2 Drawing Sheets

METHOD FOR THE COMPUTER-CONTROLLED PRODUCTION OF DENTURES

BACKGROUND OF THE INVENTION

The invention relates to a process for computer-controlled manufacture of dentures for restoration of at least one tooth or an area of the jaw or a complete jam, especially of occlusal or incisal contact conditions.

A corresponding procedure can be inferred from DE 195 18 702 A1. Here the shape of the tooth to be restored and its surroundings are recorded and electronically stored first with the aid of a measuring facility in connection with which it can be a matter of a scanning system with optical or mechanical sensors or a 3D camera. In a second step, the image is interpreted. In a third step, the restoration is constructed. Then the digitalized signals obtained by means of CAD are fed into a numerically controlled machine (CAM) in order to manufacture the denture from a block of material. Recording the shape of the area to be restored takes place at a treatment site such as a dentist's chair. In contrast, the evaluation of the measurement results as well as the manufacture of the denture itself takes place at a separate site. The CAD/CAM operations can moreover be conducted through a central computer.

A corresponding process nonetheless manifests the disadvantage that a sufficient configuration of the contact surface of the denture cannot take place. Rather, it frequently requires reprocessing.

CAD/CAM techniques for manufacturing a denture also achieve use according to EP 0 311 214 B 1, whereby for determining the shape of the denture to be constructed, a three dimensional photograph of a tooth prepared by a dentist in the mouth of the patient is generated.

From the literature citation Phillip Journal 7, pages 227 to 235, Computer-Modeled Denture with the Cicero System, an automatic manufacturing process for fixed restorations is known. Here an optical survey, sinter technology and computer-assisted manufacturing technology are used.

Underlying the present invention, among other things, is the problem of refining a process of the type mentioned at the beginning such that dentures are manufacturable by means of CAD/CM techniques in a simple manner, whereby at the same time it should be ensured that the contact surfaces of the denture have the necessary individual configuration so that a reprocessing is basically not required. Allowance should also be made for skull-related upper jaw position, especially in relation to the mandibular joint, its axis of rotation (hinge-axis) and motion pathways of the jaw joint capitulum.

SUMMARY OF THE INVENTION

In accordance with the invention, the problem is solved by the procedural steps:

Casting of upper and lower jaw for manufacturing upper jaw and lower jaw models as well as coordination of these in relation to each other by means of an articulator in a spatial orientation corresponding to the patient situation, Coordination of at least two fixed points of the upper jaw model and/or of the lower jaw model or selected reference points toward the axis of rotation of the articulator or at least two reference points allocated to this, Arrangement of the upper jaw model and arranging the lower jaw model in a measuring facility for determining the shape of the tooth, jaw area or jaw to be restored, whereby at least two fixed points are positioned in a predetermined setting to the coordinate system of the measuring facility for virtual representation of the axis of rotation of the articulator or the at least two reference points allocated to this, Digitalization of the upper and lower jaw model or components of these models, Joining together the digitizer data of the upper and lower jaw in harmony with data transmitted with the survey of the fixed points of the articulators, Construction of the denture using CAD and Manufacture of the denture using CAM.

It is especially provided that the known spatial orientation of the fixed points toward the axis of rotation (hinge-axis) of the articulator or further geometric data of the articulator are transmitted unambiguously into the measuring system through a reference element connected with the models of the upper and/or lower joint which is to be inserted only in a single position into the measuring system, and an allocation of virtual or real reference points of the axis of rotation (hinge-axis) of the articulator or further geometrical magnitudes of the articular in relation to the coordinate system of the measuring system or the data measured becomes possible.

Preferably any desired positioning of models in the measuring system can take place, and the fixed points toward the articulator are transmitted into the data record through an external reference element which is surveyed together with the models, or indirectly defines a defined position of the models, and in this way an allocation of virtual or real points of reference of the axis of rotation (hinge-axis) of the articulator or further geometrical magnitudes of the articulator toward the coordinate system of the measuring system or the measured data becomes possible.

It is provided in the refinement that more than two fixed points and/or a plane of reference are used for definition of the spatial positional reference of models toward the articulator, and are consequently, when transmitting into the measuring system upon realizing the models, the position fixed in the articulator, including the distance correlation of the models in the occlusal direction (contact points of the rows of teeth of both jaws (models)), are transmitted into the spatial orientation of the data records of upper and lower jaw.

In accordance with the invention, conventional techniques for manufacturing a denture with individually configured contact surfaces are used since for manufacturing and aligning upper and lower jaw models, customary dental recording techniques which are manageable and comprehensively tested come to be applied.

For determining the shape of the restoration, the upper jaw and lower jaw models are surveyed according to known techniques, whereby skull-related upper jaw positions can be taken into consideration through the definite coordination, for example, of the upper jaw model toward the axis of rotation of the articulator and therewith on the basis of the alignment of the lower jaw on the upper jaw of the unambiguous coordination of the lower jaw model on the axis of rotation of the articulator, and occlusal regions can be optimally recreated and processed. When surveying the upper jaw model and the lower jaw model, the axis of rotation of the articulator exists virtually, so that a clear coordination of the data exists with the result that an optimal determination of the shape of the tooth or jaw area to be restored takes place, taking into consideration an individual configuration of the contact surfaces. The use of more than two fixed points or reference planes in relation to the articulator permits transferring the position fixed in the articulator including the distance correlation of the models in the occlusal direction (contact points of rows of teeth of both jaws (models) into the spatial orientation of the data records of upper and lower jaw into the measuring system when realizing the model.

Owing to the fact that, when surveying the upper jaw model or lower jaw model, the axis of rotation as well as—if necessary—a further reference point or a reference plane exist virtually, condylar path angles and/or Bennett angles and/or Fischer angles and/or side shift can be considered for computing the restoration so that an optimal denture is manufacturable.

In other words, in the patent, operations take place with conventional methods, whereby at the same time all of the advantages of computer-controlled work processes are used.

The base plate of the upper jaw model, which is clearly positionable in the articulator as well as in a measurement facility for determining the shape of the tooth to be restored and its surroundings, is particularly used for fixed points. Scanning the upper jaw model and the lower jaw model can take place mechanically or optically.

The corresponding digitized measurement results are connected while using the known spatial orientation of at least two fixed points of the upper and lower jaw models, or selected reference points toward the axis of rotation (hinge-axis) of the articulator or allocated reference points of this with the digitized available virtual reference points of the axis of rotation (hinge-axis) of the articulator, or additional geometric data of the articulator, subsequently virtually constructed on the basis of the values of the denture so obtained, and digital signals corresponding to the constructed denture are converted by means of CAM for manufacture of the denture.

It is especially provided that for determining shape, a CCD camera is used, whereby the areas of the upper jaw model and the lower jaw model to be recorded can, for example, be illuminated with a tape pattern. Other procedures such as the gray code procedure, the phase shift process, phase measuring processes or triangulation are likewise possible.

BRIEF DESCRIPTION OF DRAWINGS

Further details, advantages and features of the invention emerge not only from the claims, the features to be gathered from these—by themselves and/or in combination—but also from the subsequent description of a preferred embodiment to be inferred from the drawings, wherein:

DETAILED DESCRIPTION OF THE INVENTION

Figure 1:
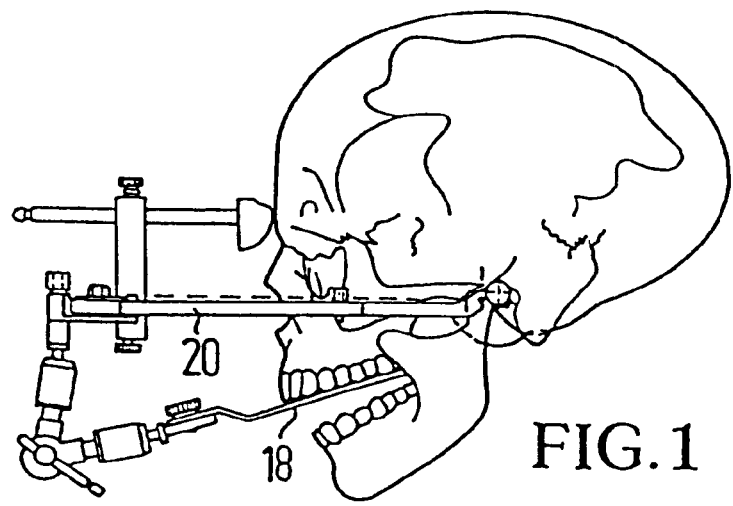
FIG. 1 Depicts a basic representation of a face bow with a bite fork positioned between the upper and lower jaw on a person, FIG. 2 Shows the face bow to be gathered from FIG. 1 for positioning an upper jaw model in an articulator, FIG. 3 Illustrates the articulator according to FIG. 2 with an articulated upper and lower jaw model, FIG. 4 Reveals an embodiment of an upper jaw model arranged in a measurement facility, and FIG. 5 Depicts a measuring facility according to FIG. 4 with virtual articulator axis of rotation.
Figure 2:
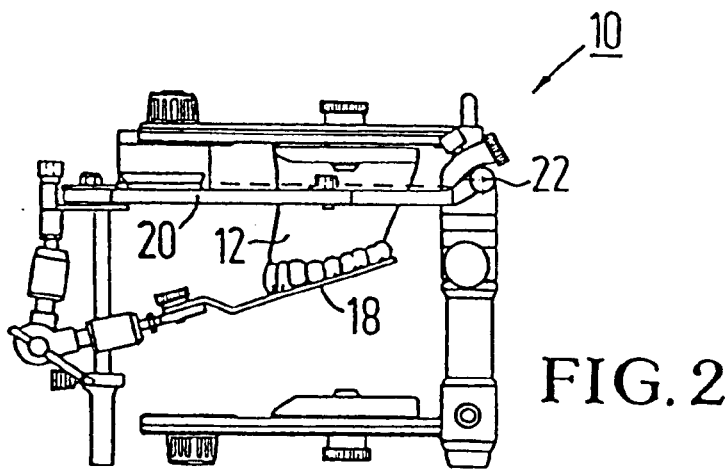
Figure 3:
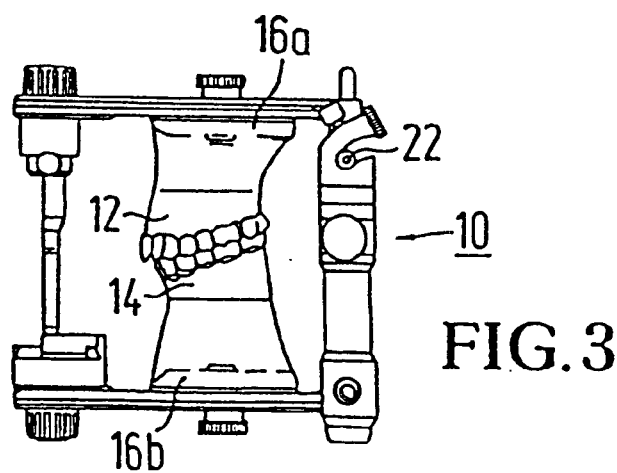

In FIGS. 1 to 3 are sufficiently known apparatus and dental recording techniques to be conducted with these are represented only rudimentarily, with which an upper jaw model 12 and toward this a lower jaw model 14 are articulated in in an articulator 10. For this purpose, for example, a jaw model with model base is produced at first by molding in the usual manner, which is joined with base plate 16a connected separably with the articulator through plaster material for assembly in the articulator, after the suitable model is aligned on a bite fork 18, which in compliance with the method represented in FIG. 1 transmits the axis of rotation (hinge-axis) of the mandibular joint of the patient through a face bow 20, for example through a device positioned pivoting in the outer auditory passage of the patient.

After removing the face bow 20, the counter bite formed by the lower jaw is then aligned on the upper jaw model 12 with the base plate 16b.

Since the upper jaw model 12 is clearly aligned toward the axis of rotation 22 of the articulator 10, the latter is also definitely positioned toward the axis of rotation owing to the once again unambiguous coordination between the upper jaw model and the lower jaw model 14.

To this extent, however, reference is made to known and prevalent recording techniques. The same applies in relation to possible eccentric motions of the lower jaw so that to this extent, reference is also made to the previously known state of the art.

Figure 5:
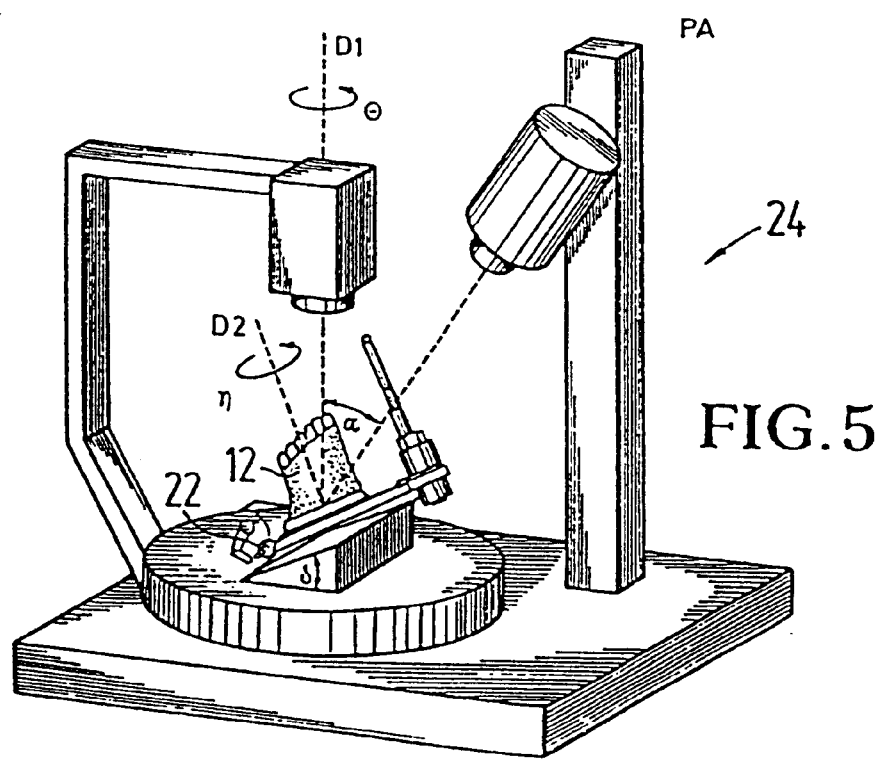

It is now provided in accordance with the invention that, by means of a measuring facility 24, the shape of a tooth or jaw area or jaw to be restored and its surroundings is determined, whereby the axis of rotation 22 of the articulator 10 is used on the basis of the known geometrical relationship between at least two fixed points of the upper and lower jaw model or selected reference points to the axis of rotation (hinge-axis) of the articulator (for example, base plate) or of these allocated reference points toward the axis of rotation (hinge-axis) of the articulator in known spatial orientation toward this in the direction of the measurement facility, as is clarified by FIG. 5. Consequently, a simultaneous coordination of the data on the axis of rotation 22 of the articulator 10, and consequently toward the axis of rotation (hinge-axis) of the mandibular joint of the patient takes place in the survey (optical in the embodiment) of the upper jaw model 12. When using reference planes (for example base plates) for transfer of the axis of rotation (hinge-axis), a correct coordination of the models is also assured in compliance with the remaining degree of freedom (rotation about the axis of rotation (hinge-axis)). Alternatively, this degree of freedom can also be defined in terms of software technology by calculation of the "contact of data records" in connection with rotation about the axis of rotation (hinge-axis). The transfer of the axis of rotation (hinge-axis) of the lower jaw to the upper jaw makes it possible for individual values with reference to the pathways of motion of the lower jaw (condylar pathway angle of inclination, Bennett angle, Fischer angle, side shift) also to be considered to construct the denture on the basis of the digitized data obtained by the measurement.

In other words, a spatial coordination of the upper jaw model 12 and the lower jaw model 14 takes place on the basis of the virtually laid down axis of rotation 22, although the lower jaw model 14 and the upper jaw model 12 are measured independently of each other.

It is alone decisive that a definite reference between one of the models 12 and 14 to the axis of rotation 22 or reference points allocated to this exists and then to the coordinate system of a measurement facility 24. This takes place preferably over the base plate 16a, 16b, which is clearly positioned in the measurement facility 24 represented in FIGS. 4 and 5 and in this way makes possible a definite coordination toward the axis of rotation 22 and corresponding reference points of the articulator 10.

Figure 4:
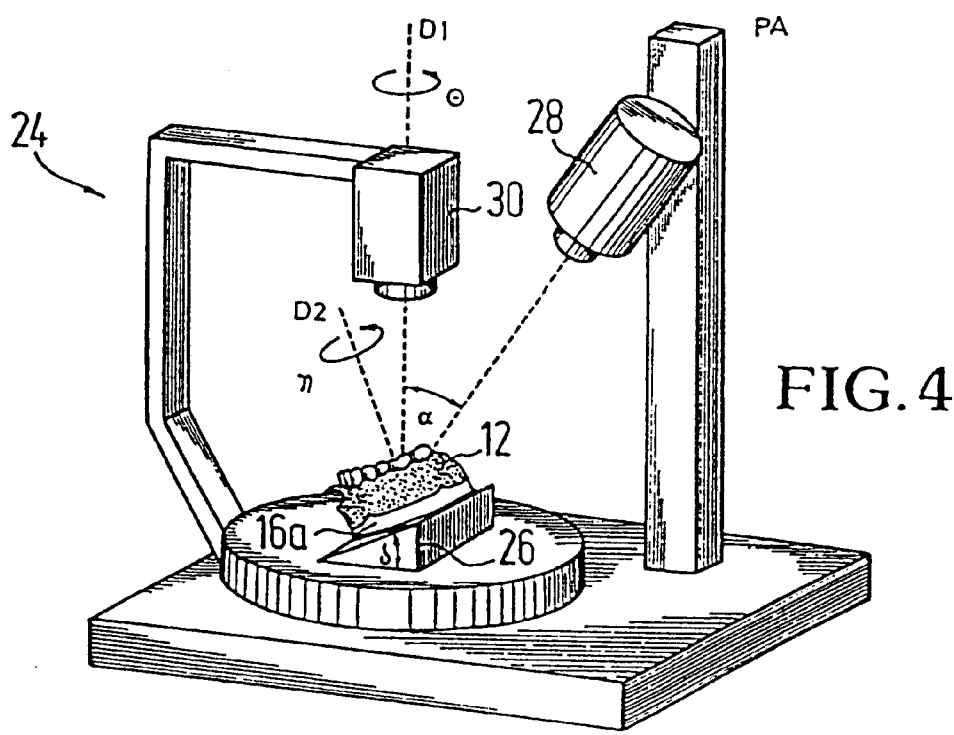

In the embodiment of FIGS. 4 and 5, the upper joint model 12 is arranged on a wedge-shaped mounting 26, in order then to act upon the area of the tooth or jaw to be restored, for example with strip light which is beamed from a strip projector 28. The image of the strip pattern is determined, for example, with a CCD camera, whereby for example the partial information is obtainable through distortion of the strip pattern.

For spatial measurement of models 12,14, the CCD camera 30 can be rotated about the axis D1. Correspondingly, there also exists the possibility of rotating the model 12 about axis D2. Through these measures, a spatial recording of the shape of the model 12 is made possible.

The lower jaw model 14 is correspondingly measured, which likewise shows a definite coordination toward the virtually axis of rotation 22 of the articulator also recorded on the basis of the clear coordination toward the upper jaw model 12 after being articulated in.

The values so ascertained are processed by means of a CAD system in order to construct a denture. Subsequently, the production of a denture takes place in the usual manner with CAM (computer aided manufacturing).

Other possibilities for measuring the upper and lower jaw model 12 and 14, such as, for example, stereophotogrammetric processes using conventional cameras with light guides and conventional film material and subsequent digitization or preparation of recordings of each preparation by means of CCD cameras, whereby strip patterns can be imaged for ascertaining information on depth, are likewise possible. Mechanical digitization is to be indicated as a further measuring possibility.

I claim:

1. A method for computer-controlled production of dentures for the restoration of at least a tooth, a jaw region or a complete jaw, comprising the steps of:

taking impression of an upper jaw and a lower jaw for manufacturing an upper jaw cast and a lower jaw cast as well as coordination of these in relation to each other by means of an articulator in a spatial orientation corresponding to a patient situation;

Coordinating of at least two fixed points of the upper jaw cast or of the lower jaw cast or at least two fixed points or the cast's mounting device toward the axis of rotation of the articulator or at least two reference points allocated to this;

Arranging the upper jaw cast and the lower jaw cast in a measuring facility for determining the shape of the tooth, jaw region, or the complete jaw to be restored, whereby at least two fixed points are positioned in a predetermined setting toward the coordinate system of the measuring facility for virtual representation of the axis of rotation of the articulator or the at least two reference points allocated to this;

Digitizing the upper and lower jaw casts or components of the upper and lower casts, taking into consideration the virtual axis of rotation of the articulator or the at least two reference points;

Joining together the digitized data of the upper jaw and the lower jaw according to the data transmitted with the survey of the fixed points of the articulators;

designing the denture using CAD; and

Manufacturing the denture using CAM.

2. The method of claim 1, characterized in that the known spatial orientation of the fixed points toward the axis of rotation (hinge-axis) of the articulator or additional geometric data of the articulator is transmitted definitely into the measurement system through a reference element joined with the models of the upper and/or lower jaw which is to be inserted into the measurement system only in a single position, and in this way a coordination of virtual or real reference points of the axis of rotation (hinge-axis) of the articulator or additional geometric magnitudes of the articulator to the coordinate system of the measuring system or the measured data becomes directly or indirectly possible.

3. The method of claim 1, characterized in that any desired positioning in the measurement takes place, and the fixed points in relation to the articulator are transferred into the data records through an external reference element which is surveyed together with the upper and lower casts or indirectly defines a direct position of the upper and lower casts toward the measurement facility, and in this way, a coordination of virtual or real reference points of the axis of rotation (hinge-axis) of the articulator or further geometrical magnitudes of the articulator to the coordinate system of the measuring system or the measured data becomes directly or indirectly possible.

4. The method of claim 3, characterized in that more than two fixed points and/or a reference plane are used for definition of the spatial position of the casts to the articulator and consequently, when converting the casts into the measuring facility, the position fixed in the articulator, including the distance reference of the casts in the occlusal direction (contact points of the teeth of both jaws (casts)) is transmitted into the spatial orientation of the data records of upper and lower jaw.

5. The method of claim 4, characterized in that in addition to data representing the shape of the upper jaw cast and/or the lower jaw cast, taking into consideration the virtual axis of rotation of the articulator or the points of reference allocated to this, condylar pathway angles of inclination and/or Bennet angles and/or Fischer angles and/or side shift are incorporated for designing of the denture.

6. The method of claim 5, characterized in that mounting device of the upper jaw cast in the articulator is used as the fixed points.

7. The method of claim 6, characterized in that the upper jaw cast and/or the lower jaw cast are mechanically and/or optically digitize.

8. The method of claim 8, characterized in that a CCD camera is used for determining the shape of the tooth or jaw region to be restored.

9. The method of claim 8, characterized in that, for measuring the tooth or jaw region, this is irradiated with gray code or structured light.

10. The method of claim 9, characterized in that a stereophotogrammetric procedure is used for determining the shape of the tooth or jaw region to be restored.

11. The method of claim 4, characterized in that the digitized data obtained form the upper jaw cast and/or the lower jaw cast and the data of the virtual axis of rotation present in digitized values are coordinated, then the denture is virtually constructed and corresponding digital signals are converted for the constructed denture by means of CAM for manufacture of the denture.

12. The method of claim 3, characterized in that mechanical or optical positioning aids are used for the transfer of the hinge-axis.

13. The method of claim 12, characterized in that, after alignment of the data records of the upper and lower jaw casts by means of the axis of rotation (hinge-axis), remaining degree of freedom is defined by computation of intersections of the data records of upper and lower jaws or graphic representation of these intersections in the CAD software.

* * * * *